United States Patent [19]

Moran

[11] 4,039,287
[45] Aug. 2, 1977

[54] REACTION CONVEYOR ASSEMBLY IN AN AUTOMATIC CHEMICAL TESTING APPARATUS

[75] Inventor: John J. Moran, Houston, Tex.

[73] Assignee: Hycel, Inc., Houston, Tex.

[21] Appl. No.: 725,237

[22] Filed: Sept. 21, 1976

[30] Foreign Application Priority Data

Mar. 17, 1976 United Kingdom ............... 10685/76

[51] Int. Cl.$^2$ ......................... G01N 1/10; G01N 33/16
[52] U.S. Cl. ..................................... 23/253 R; 23/259
[58] Field of Search ................. 23/230 R, 253 R, 259; 141/130

[56] References Cited

U.S. PATENT DOCUMENTS

| 3,644,095 | 2/1972 | Netheler et al. | 23/259 |
| 3,728,079 | 4/1973 | Moran | 23/259 X |
| 3,854,879 | 12/1974 | Figueroa | 23/230 R |
| 3,883,305 | 5/1975 | Hoskins et al. | 23/253 R |
| 3,985,508 | 10/1976 | Williams | 23/253 R |

*Primary Examiner*—R.E. Serwin
*Attorney, Agent, or Firm*—Timothy L. Burgess; Robert P. Cogan

[57] ABSTRACT

In an automatic chemical testing apparatus including a reaction conveyor carrying rows of reaction containers from a sample dispensing station through a reaction station and to an analysis station, the improvement is provided in which slats containing the reaction containers are linked together to form a reaction loop conveyor without the need for a separate chain. The loop path includes first and second apexes and a forward path between the apexes. Guideways are provided to maintain the reaction container slats in an upright disposition between the forward path and the apexes. Further, a conveyor housing assembly is provided housing incubation means, reaction container washing means and means for driving the conveyor directly.

19 Claims, 9 Drawing Figures

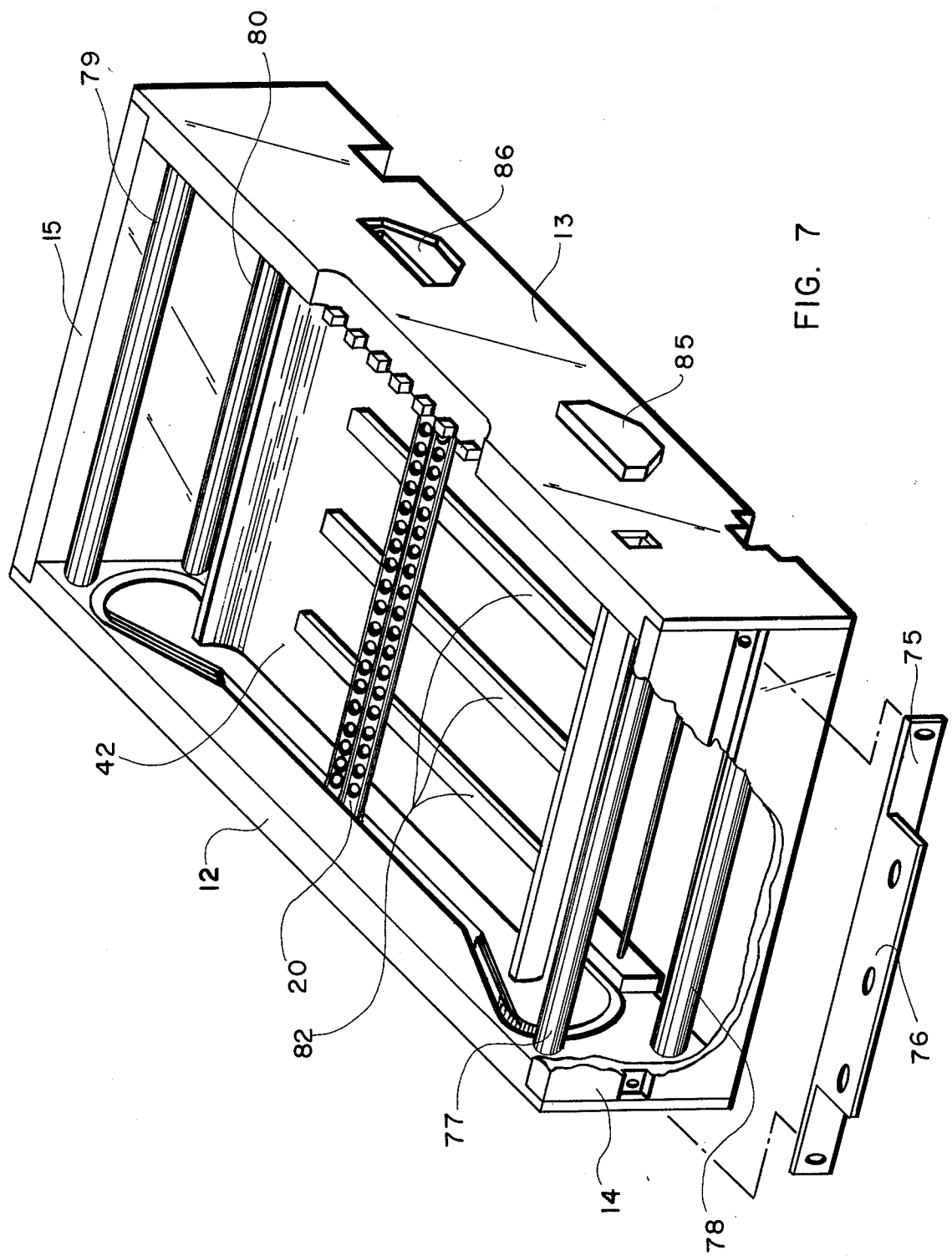

REACTION CONVEYOR ASSEMBLY IN AN AUTOMATIC CHEMICAL TESTING APPARATUS

BACKGROUND OF THE INVENTION

The present invention relates to automatic chemical testing apparatus, and more particularly to a reaction conveyor assembly included therein.

The present invention relates to improvements in the type of automatic chemical testing apparatus disposed in U.S. Pat. Nos. 3,728,079 and 3,762,879 issued respectively on Apr. 17, 1973 and Oct. 2, 1973 both to John J. Moran and assigned to the assignee herein, the disclosures of which are incorporated by reference. In apparatus of that type, aliquots of samples to be analyzed, e.g., human serum, are dispensed into reaction containers in individual rows, and the rows are indexed through a series of positions including passing through incubation means and stations at which reagents are added to the samples and further indexed to readout means at which reacted contents in reaction containers are aspirated and analyzed for the concentration of particular substances in the samples.

The loop conveyor, which may also be called the reaction conveyor, is a very important part of this apparatus. It is desirable to reduce the complexity of such assemblies to reduce expense to construction and maintenance and to increase reliability and effectiveness in operation. For example, U.S. Pat. No. 3,799,794 to Jones discloses an apparatus far more complex than that contemplated by the present invention for moving reaction container rows along a conveyor path.

It is also desirable to provide for other functions such as cleaning of reaction containers and for cooperation with other analyzer components.

SUMMARY OF THE INVENTION

It is therefore an object of the present invention to provide for an improved reaction conveyor in an automatic chemical testing apparatus which is simplified in construction.

It is also an object of the present invention to provide an efficiently constructed reaction conveyor assembly including conveyor means, incubation means, and drive means for the conveyor.

It is a more specific object of the present invention to provide a conveyor assembly of the type described in which the conveyor is directly driven without the need for an intermediate drive chain.

It is also an object of the present invention to provide a conveyor assembly of the type described for facilitating cooperation of the conveyor means with other testing apparatus components.

Briefly stated, in accordance with the present invention, there is provided an improved reaction conveyor assembly in which reaction conveyor rows are linked together and directly driven. Conveyor guideways in conveyor housing means maintain conveyor rows in an upright position between first and second apexes and a forward path therebetween. The conveyor housing also supports incubation means, drive means and further means for cooperating with other components of the automatic chemical testing apparatus.

BRIEF DESCRIPTION OF THE DRAWINGS

The means by which the foregoing objects and features of invention are achieved are pointed out in the claims forming the concluding portion of the specification. The invention, both as to its organization and manner of operation, may be further understood by reference to the following description taken in connection with the following drawings.

Of the drawings:

FIG. 7 is an axonometric view of the conveyor housing; and

DESCRIPTION OF THE PREFERRED EMBODIMENT

Figure 1:
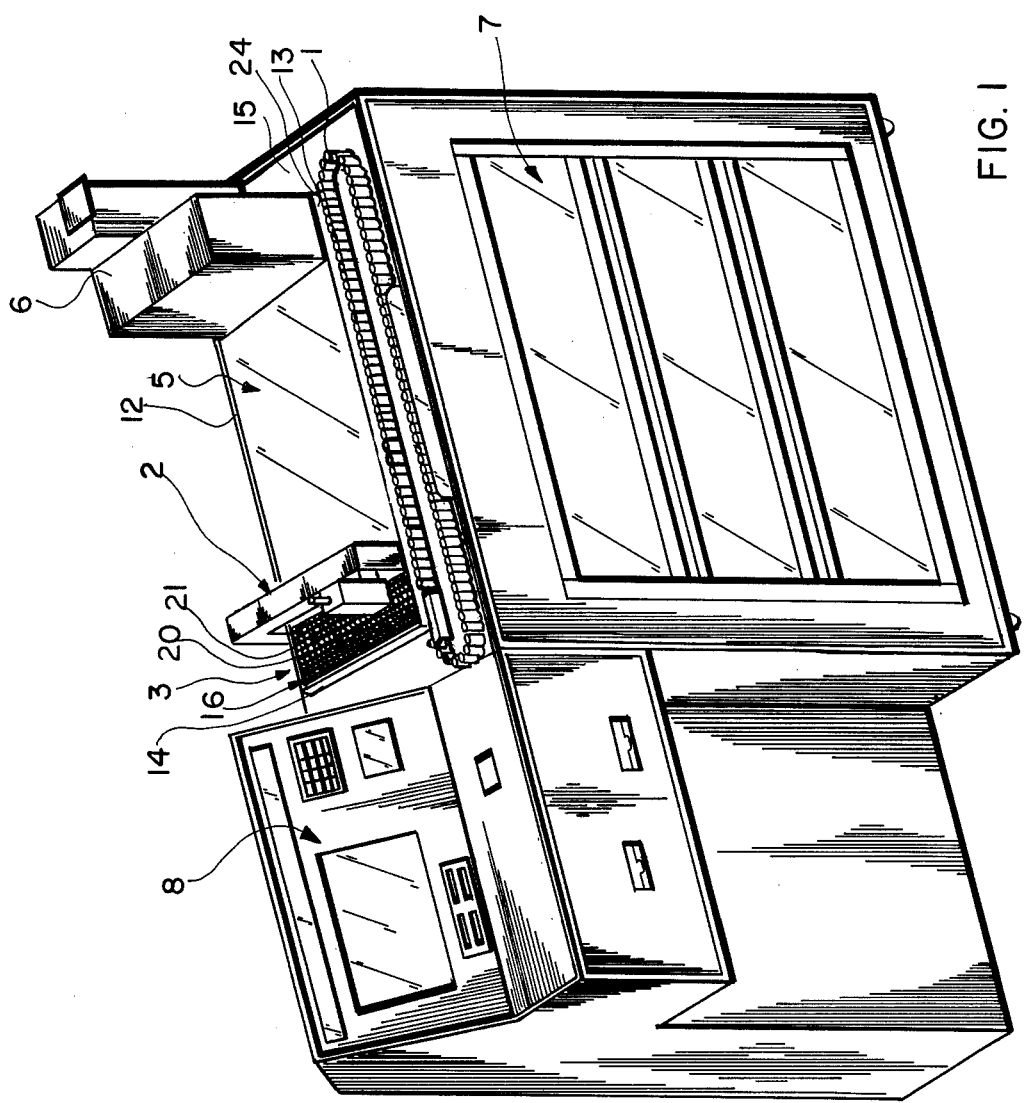
FIG. 1 is an axonometric illustration of a chemical testing apparatus constructed in accordance with the present invention.

Referring to FIG. 1, there is illustrated in an axonometric form a chemical testing apparatus of the type described in the above-cited patents to Moran to which reference should be had for description of further details of construction and operation. Briefly stated, samples from a sample source 1 are provided to sample dispensing means 2 which provides aliquots of serum to individual reaction containers described below. The sample source 1 of the present embodiment is an alternative to that described in the above-cited patents and is further described in co-pending patent application, Ser. No. 725,260 filed Sept. 21, 1976. As will be further described below, the rows are indexed to incubation and reaction dispensing stations 5 to analysis means 6. Reagents are provided from a reagent source 7. In the present embodiment, keyboard control and display means 8 replace the control and recorder means as described in the above-cited patents.

The conveyor means of the present embodiment comprises a conveyor housing 10 having opposite longitudinally extending walls 12 and 13 joined at their longitudinal ends by transversely extending opposite walls 14 and 15. The conveyor housing 10 supports a conveyor 16 formed of individual slats 20, which may also be called slats or sections, each supporting a plurality of reaction containers 21 therein. The conveyor housing 10 is mounted to and through an upper surface 24 of the chemical testing apparatus. The sample dispensing means 2 are supported to the opposite walls 12 and 13 of the conveyor housing 10, and the readout means 6 are also supported thereon. Thus the conveyor housing 10 not only serves the function of supporting the conveyor 16 but also supports the other components as described above.

Figure 2:
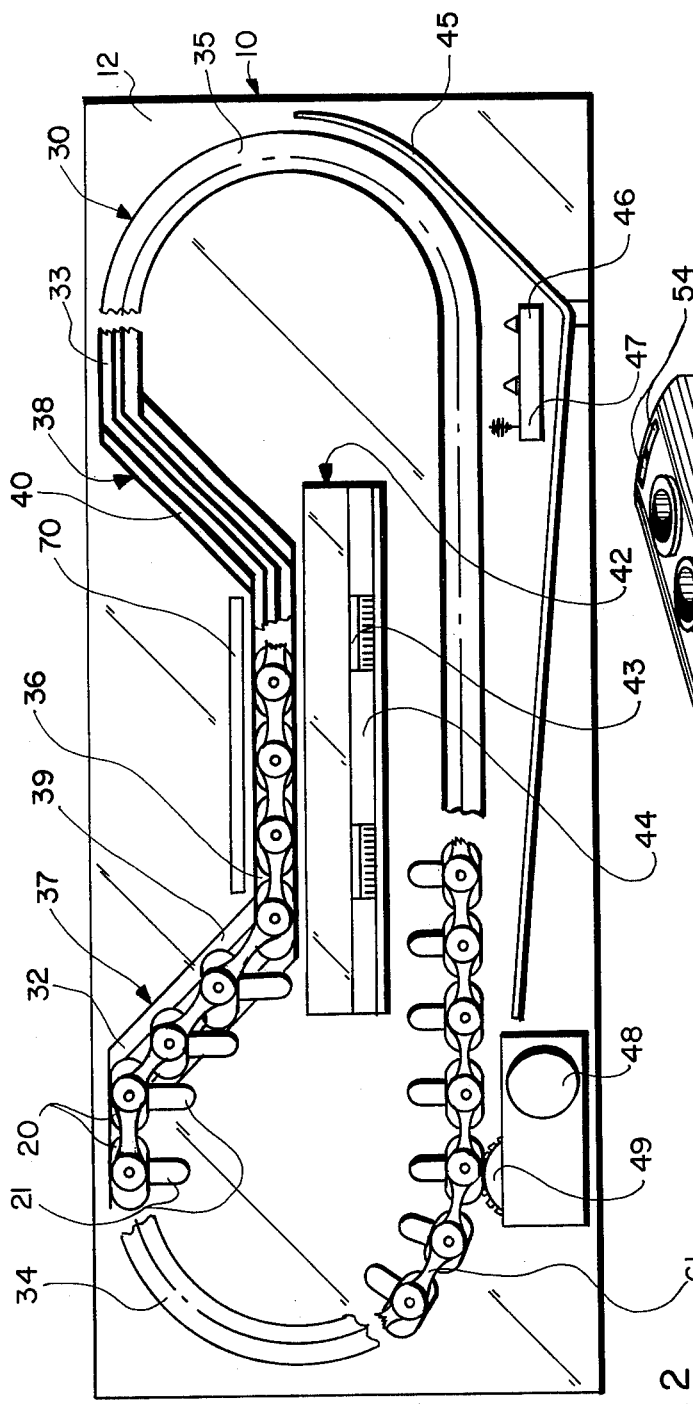
FIG. 2 is a mechanical schematic diagram of a longitudinal cross-section of a reaction conveyor according to the present invention taken along lines 2—2 of FIG. 1.
Figure 8:
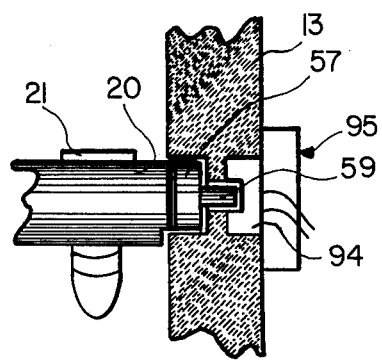
FIGS. 8 and 9 are partial cross-sectional views respectively taken along lines 7—7 and 8—8 of FIG. 7, respectively illustrating cooperation of the assembly of FIG. 4 in a conveyor guideway and further illustrating a detail of the conveyor assembly.

In FIG. 2, which is a mechanical schematic representation illustrating the conveyor and conveyor path, a guideway 30 in the wall 12 defines the conveyor path. A guideway 30 is also performed in the wall 13 differing only as described with respect to FIG. 8 below. Therefore, FIG. 2 may be regarded as an illustration of guideways in both the walls 12 and 13. The conveyor path, defined by the guideways 30, comprises a lower, return path 31, vertically and second apexes 32 and 33, first and second contours 34 and 35 respectively joining the apexes 32 and 33 to the lower path 31. The conveyor path 30 further comprises an upper, forward path 36 having a straight line portion 37 connecting it to the apex 32 and another straight line portion 38 connecting the upper path 36 to the apex 33. The guideway 30 through its entirety includes a keyway cut into the walls 12 and 13 equal to the thickness of each slat or row 20. Thickness is measured in the direction in which the reaction containers 21 extend. Additionally, the straight line portions 37 and 38 include further grooves 39 and 40 respectively surrounding the portions 37 and 38 which are the width of the slats 20. Width is the dimension of the row 20 in the direction of travel. As further described below, in the straight line portion 37 and 38, the rows 20 are pivotally supported. Due to the dimensioning, camming action of the edges of the rows 20 against the grooves 39 and 40 results. The reaction containers 21 mounted in the slat 20 provide a gravitational force assisting in maintaining the rows 20 vertically disposed.

In the above system, the apex 32 is preferably positioned adjacent the sample dispensing means 2 (FIG. 1). The analysis means preferably withdraw reactive sample material from a position in the vicinity of the intersection of the forward path 36 with the straight line path 38.

The slats 20 are carried in the upright manner in the forward portion 36 and in the contour 35 are inverted for the purpose of dumping reacted contents from the reaction containers 21. In the return path 31, they are inverted, being brought back to the upright position at apex 32 by travel through the contour 34. The walls 12 and 14 support the conveyor and surround incubation means 45 positioned with respect to the upper path 36 such that the reaction containers 21 are incubated and remain at a temperature determined by the incubation means 42. In the preferred embodiment, the incubation means 42 comprises a thermostatically controlled water bath.

The incubation means 42 may include mounted to its lower surface heating means 43 surrounded by insulation means 44. The heating means 43 preferably comprise Peltier effect heaters and heat sink fins mounted thereto, and the insulation means preferably comprises a sheet of polyurethane foam having cut-out portions in registration with each of the heating means. A trough 45 extends between and is mounted to the walls 12 and 13 below the conveyor 16 for receiving and providing an outlet for used liquid dumped from the conveyor 16. Cleaning means 46 and drying means 47 are supported to the conveyor housing 10 intermediate the conveyor 16 and the trough 45 for cleaning reaction containers 21 in the return path 31. A reagent dispensing plat 70 is described further below with respect to FIG. 6 and is mounted to the walls 12 and 13 above the forward path 36 of the conveyor 16.

A further illustrated in FIG. 2, drive means 48 include sprocket means 49 for driving the conveyor 10 directly as further described below.

Figure 3:
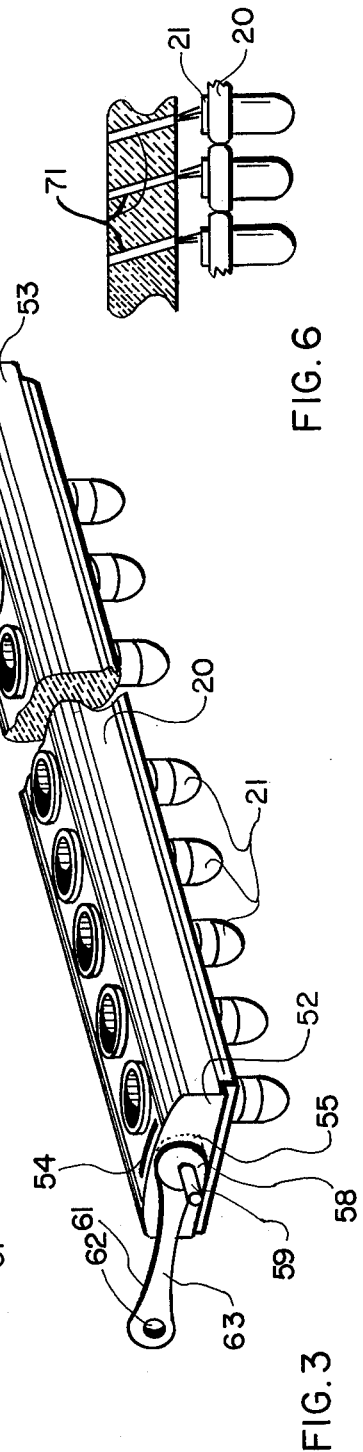
FIG. 3 is an axonometric illustration of a slat comprising one row of the conveyor.
Figure 4:
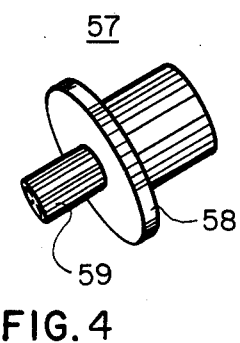
FIG. 4 is a detail of a button and pin mounted in a first end of a conveyor row.
Figure 5:
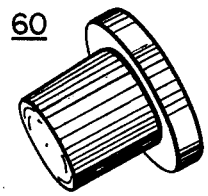
FIG. 5 is a detail view of a button mounted in an opposite end of a conveyor slat for cooperation with guideways.

An individual slat 20 is illustrated in FIG. 3 in axonometric form. Each of the slats 20 may be constructed identically. The slats 20 extend in a transverse direction for travel in a longitudinal direction. Apertures 50 are formed spaced along a transversely extending axis for receiving one of the sample cups 21 which are each preferably press-fit therein. The opposite ends of each slat 20 are formed to comprise keys 52 and 53 for cooperating and fitting in the opposite keyways 30. In each slat transversely displaced away from keys 52 and 53, sprocket recesses 54 are formed for cooperating with the drive means 48. The key 52 is formed with an aperture 55 for receiving a button assembly 57. The button assembly 57, further illustrated in FIG. 4, comprises a first portion 56 received in the aperture 55 and second portion 58 comprising a cylindrical projection of "button" extending transversely from the end thereof and which is dimensioned to have a diameter substantially equal to the vertical width of the keyway 30. In this manner, pivotal mounting of the slat 20 in the sections 38 and 39 is provided. A pin portion 59 projects transversely from the button 58 for use as described with respect to FIG. 8. As seen in FIG. 5, a similar pin assembly 60 is provided for mounting in the key 53 which does not have a pin portion. The pin assemblies 57 and 60 also serve as retaining means for links 61 (FIG. 2) with which the conveyor is linked together. The links 61 each have eyelet portions 62 linked by a center portion 63. The center to center distances of the eyelet portions 62 are equal to the distances between the button assemblies 57 and 60 of adjacent slats 20. Consequently, when assembled, as indicated in FIG. 2, the conveyor is an assembly which may be driven directly and does not require an additional chain for cooperating with the drive means 48.

When the conveyor thus described is assembled, reaction containers 21 in transverse registration with successfully longitudinally placed slats 20 form columns. Each column may also be referred to as a channel and be dedicated for receiving reagents and delivering reactive contents to analysis means for detecting one particular substance in the sample material.

Figure 6:
FIG. 6 is a partial cross-sectional view illustrating means for maintaining reagent lines in the conveyor assembly.

It is further of great significance to note that the reagent nozzle plate 70 illustrated in partial cross-sectional form in FIG. 6 is mounted between the walls 12 and 13 and positioned in registration with and above the forward path 36. The plate 70 has a plurality of apertures 71 therein, each in registration with the position of a reaction container 21 when it has been indexed to one of the predetermined positions. The purpose of the plate is to receive reagent injecting lines and provide reagent supply along a fixed trajectory into each reaction container 21. It is important to select the trajectory of the reagent stream dispensed into each reaction cup to provide for optimal mixing of reagent and sample for improved results. The plate 70 is positioned such that, and the apertures 71 are angled such that a preselected trajectory of reagent dispensing of each reaction container is provided for. It should be realized that not every aperture 71 need be connected to a source of reagent supply. The conveyor housing 10 thus cooperates with the conveyor to provide for improved reagent delivery. The apertures 71 are arranged in columns and rows as are the reaction containers 21.

Further details and advantages in the preferred construction of the conveyor housing 10 are illustrated with respect to FIG. 7 which is an axonometric view of the conveyor housing 10 with the conveyor 16 and plat 70 removed therefrom. In the illustration of FIG. 7, the wall 14 is partially broken away to form a better illustration of further detail described below.

A mounting bracket 75 is shown affixed to the transversely extending wall 14 including a flange 76 for mounting to the upper surface 24. An identical mounting bracket 75 not seen in the projection of FIG. 7 is fixed to the wall 15.

First and second transversely extending spacer bars 77 and 78 are provided fixed at opposite transverse ends in the walls 12 and 13 adjacent the wall 14. Similar spacer bars 79 and 80 having opposite transverse ends fixed in the walls 12 and 13 adjacent the wall 15 are provided. The spacer bars 77–80 assist in maintaining transverse dimensional tolerances even in the presence of widely varying temperature conditions. Binding of the rows 20 in the guideways 30 is one problem which is avoided.

Referring in further detail to the incubation means 42, in the upper surface thereof, longitudinally disposed upwardly extending bosses 82 are formed. The bosses 82 are each positioned to be in registration with at least a longitudinal portion of a column of reaction containers 21. The incubation means 42 are positioned and the bosses 82 are dimensioned to provide support for reaction containers 21 in their longitudinal path. Since support is provided, the slats 20 are prevented from bowing along their transverse dimension. One benefit of this construction is that binding of the keys 52 and 53 in the keyways 30 is further avoided.

Air manifold means 85 are provided, each mounted to apertures 86 in the wall 13. The air manifold means and apertures provide for directing a source of flowing air mounted below the incubation means 42 across the heating means 43 for assisting in regulating the temperature of the incubation means 42.

An aperture 90 is formed in the wall 13 communicating with the keyway 30 therein. Further reference should be had to FIG. 8, which is a partial cross-sectional view illustrating the key 52 of a slat 20 in the keyway 30 of the wall 13. A further keyway portion 92 extends transversely from the keyway 30 for receiving the pin 59 (FIGS. 3 and 4) throughout the travel of the conveyor 16. The aperture 90 is formed to receive a photosensor means 94 mounted for having a light path defined therein intercepted by at least an end portion of a pin 59 passing therethrough. The photosensor means 94 comprises optical limit switching means for measuring the travel of conveyor rows. The optical limit switching means 95 cooperates with the drive means 48 to assure precise indexing of the conveyor 16.

Figure 9:
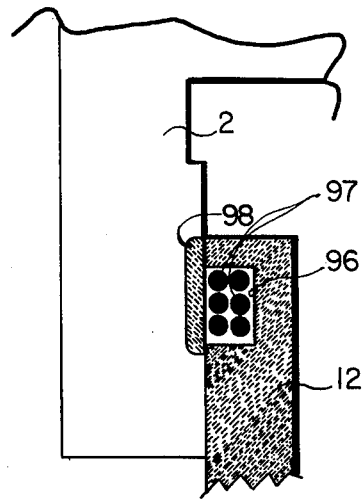

FIG. 9 is a partial cross-section view of the wall 12 at a point at which the sample dispensing means 2 (FIG. 1) is mounted thereto. A recess 96 formed in the wall 12 for receiving wires 97 for coupling to the keyboard, terminal and control means 8 (FIG. 1). Cover means 98 mating with an outside (transversely away from the conveyor 16) face of the wall 12 may be provided. Thus wiring harness means are provided for in the wall 12, further aiding in cooperation of the conveyor housing 10 with components mounted thereto. FIG. 9 is also illustrative of provision for carrying other wires if desired to provide for necessary interactions in an automatic chemical testing apparatus.

The above specification has been written with a view toward enabling those skilled in the art to make many changes in the specific embodiment disclosed to provide a reaction conveyor and reaction conveyor assembly constructed in accordance with the present invention.

What is claimed as new and desired to be secured by Letters Patent of the United States is:

1. In a chemical testing apparatus having a dispensing means for dispensing sample aliquots to reaction containers, means for supply reagents to reaction containers and a readout station for aspirating reaction container contents and analyzing the contents, conveyor means comprising: an endless loop conveyor having a path of travel including a first longitudinal upper path, a second longitudinal lower path, first and second apexes adjacent opposite ends of the upper path and higher than the upper path, substantially straight line portions connecting the apexes to the upper path and contours connecting the apexes to the lower path, said conveyor comprising sections each extending transversely and defining a row, said sections supporting reaction containers which are disposed uprightly in the upper path and inverted during travel in the lower path; said section each having locations such that corresponding locations of reaction containers in adjacent sections define columns; link means secured between adjacent sections, and drive means engaging at least one said section for directly driving said conveyor.

2. A conveyor means according to claim 1 further comprising a conveyor housing having first and second walls at transverse ends of said sections for surrounding and supporting said conveyor, said conveyor walls each including a conveyor guideway formed therein, the portion of said guideways defining said path of travel, said upper path and said lower path having a vertical width equal to the thickness of said sections, said guideways in said portions connecting said apexes to said upper path having a width in horizontal cross-section equal to the longitudinal length of a section for providing camming action against transversely disposed edges of said sections as said conveyor moves in a longitudinal direction, whereby said sections are maintained in a substantially upright position between said upper path and each of said apexes.

3. Apparatus according to claim 1 further comprising an incubation means surrounded in a longitudinal direction by said conveyor and positioned such that said reaction containers travel through said incubation means while traveling in said upper path.

4. Apparatus according to claim 3 wherein said incubation means comprises a substantially flat lower surface lying in a plane parallel to a plane defined by the upper path and having raised portions thereon in registration with selected columns defined by reaction containers for supporting said reaction containers, whereby bending of said sections is prevented.

5. Apparatus according to claim 4 wherein said incubation means comprises a water bath.

6. Conveyor means according to claim 5 wherein said first and second laterally displaced walls are joined at their ends by longitudinally displaced walls and wherein said walls further house trough means for receiving contents from inverted reaction containers from said conveyor.

7. Apparatus according to claim 6 wherein said drive means are mounted to said conveyor housing and wherein said conveyor drive means comprising a sprocket drive for meshing with a selected conveyor section whereby drive force is applied to the entire conveyor.

8. Conveyor means according to claim 2 further comprising a further recess, in a guideway in one said wall, pin means projecting from one transverse end of each of said sections and extending into said further recess, and means for monitoring the travel of said conveyor responsive to positioning of said pin means.

9. Conveyor means according to claim 8 wherein said means for monitoring comprises photosensor means mounted in a recess in said one wall communicating with said further recess and defining a light path intersecting the path of said pin means.

10. Conveyor means according to claim 2 wherein said reagent dispensing means and said analysis means are mounted to said walls.

11. In a chemical analyzer having a dispensing means for dispensing sample aliquots to reaction containers, means for supplying reagents to reaction containers and a readout station for aspirating reaction container contents and analyzing the contents, reaction conveyor housing means comprising: an endless loop conveyor and opposite walls having guideways formed therein for receiving and defining a path of travel including a first longitudinal upper path, a second longitudinal lower path, first and second apexes adjacent opposite ends of the upper path and higher than the upper path, substantially straight line portions connecting the apexes to the upper path and contours connecting the apexes to the lower path, said guideways for supporting reaction containers mounted in conveyor sections disposed uprightly in the upper path and inverted during travel in the lower path, the portions of said guideways defining said contours, said upper path and said lower path having a vertical width equal to the thickness of a section, to be supported, and said guideways in said portions connecting said apexes to said upper path having a width in horizontal cross-section equal to the longitudinal length of a section for providing camming action against transversely disposed edges of said sections as said conveyor moves in a longitudinal direction, whereby said sections will be maintained in a substantially uprightly position between said upper path and each of said apexes.

12. Apparatus according to claim 11 further comprising an incubation means surrounded in a longitudinal direction by said conveyor and positioned such that said reaction containers travel through said incubation means while traveling in said upper path.

13. Apparatus according to claim 12 wherein said incubation means comprises a substantially flat lower surface lying in a plane parallel to a plane defined by the upper path and having raised portions thereon in registration with selected columns defined by reaction containers for supporting reaction containers.

14. Apparatus according to claim 13 wherein said incubation means comprises a water bath.

15. Apparatus according to claim 14 wherein said water bath comprises a lower surface and heating means mounted thereto and wherein air manifold means are provided in one of said walls for directing flowing air from a source across said heating means.

16. Conveyor means according to claim 15 wherein said first and second laterally displaced walls are joined at their ends by longitudinally displaced walls and wherein said walls further house trough means for receiving contents from inverted reaction containers from the conveyor.

17. Apparatus according to claim 16 further comprising said drive means mounted to said conveyor housing for driving the conveyor.

18. Conveyor housing means according to claim 17 further comprising a further recess in a guideway in one said wall for receiving pin means projecting from one transverse end of a section of the conveyor for extending into said further recess, and means for monitoring the travel of said conveyor responsive to positioning the pin means.

19. Conveyor housing means according to claim 18 wherein said means for monitoring comprises photosensor means mounted in a recess in the one said wall and defining a light path for interception by the pin means.

* * * * *